Figure 1:
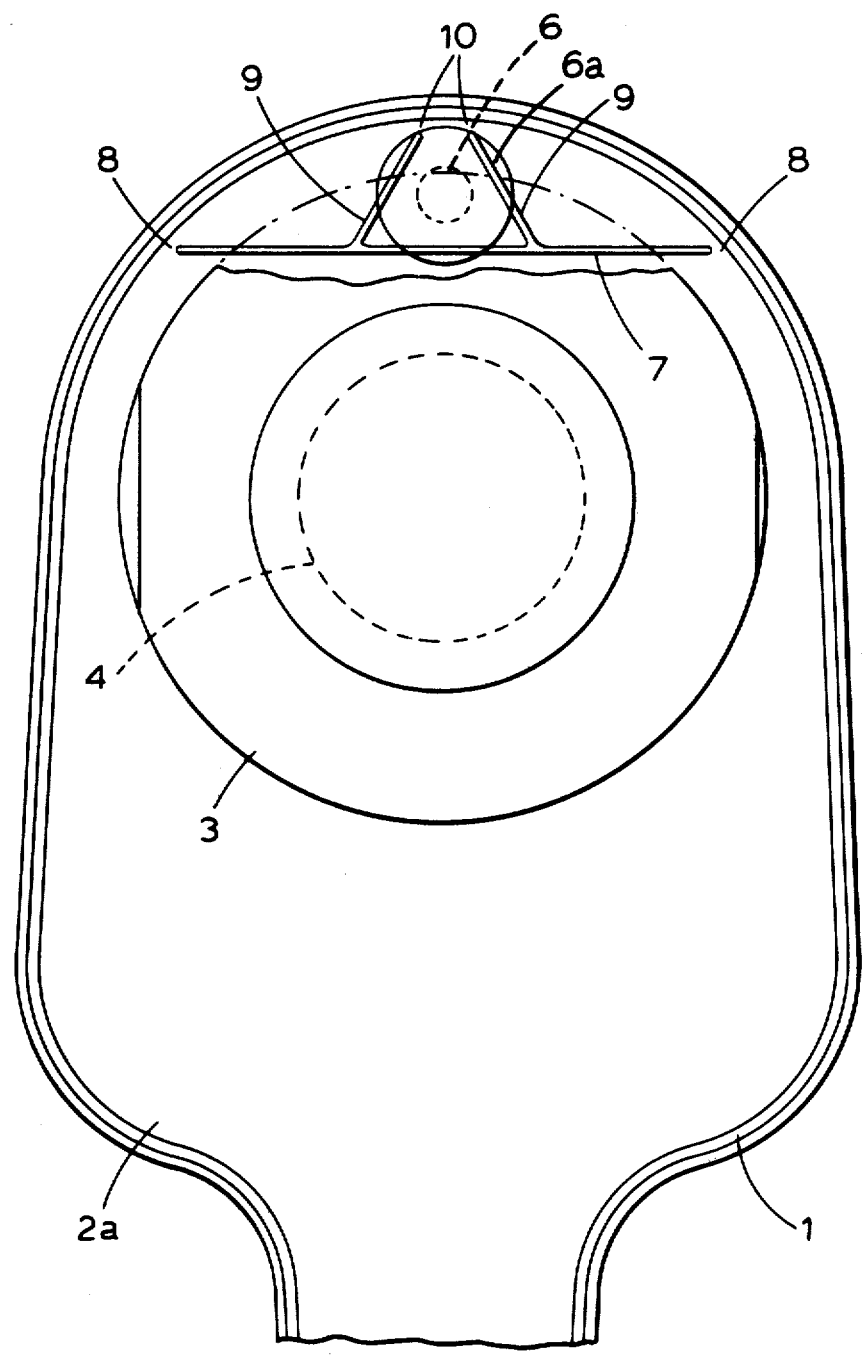

United States Patent [19]

Briggs et al.

[11] 4,387,712
[45] Jun. 14, 1983

[54] SURGICAL COLLECTION BAGS

[75] Inventors: Peter J. Briggs, Sompting; Steven Carpenter, Chichester, both of England

[73] Assignee: Matburn (Holdings) Limited, London, England

[21] Appl. No.: 57,700

[22] Filed: Jul. 16, 1979

[30] Foreign Application Priority Data

Jul. 19, 1978 [GB] United Kingdom ............ 30349/78
Nov. 16, 1978 [GB] United Kingdom ............ 44769/78

[51] Int. Cl.³ .............................................. A61F 5/44
[52] U.S. Cl. .......................... 604/333; 128/DIG. 24
[58] Field of Search ........ 128/283, 295, 272, DIG. 24

[56] References Cited

U.S. PATENT DOCUMENTS

| 3,055,368 | 9/1962 | Baxter | 128/283 |
| 4,185,630 | 1/1980 | Neumeier | 128/283 |
| 4,203,445 | 5/1980 | Jessup et al. | 128/283 |

FOREIGN PATENT DOCUMENTS

| 2620129 | 11/1976 | Fed. Rep. of Germany | 128/283 |
| 1295252 | 11/1972 | United Kingdom | 128/283 |
| 1337697 | 11/1973 | United Kingdom . | |
| 1379464 | 1/1975 | United Kingdom . | |
| 1405032 | 9/1975 | United Kingdom . | |
| 1445092 | 8/1976 | United Kingdom . | |

Primary Examiner—Kyle L. Howell
Assistant Examiner—J. L. Kruter
Attorney, Agent, or Firm—McAulay, Fields, Fisher, Goldstein & Nissen

[57] ABSTRACT

A surgical collection bag for post operative use having two opposed walls, secured together by a perimeter weld. One of the walls has an inlet opening through which the contents of the intestine of a patient can flow into the interior of the bag. The same wall also has a vent which is impervious to solid material and liquid from the intestine of the patient but which is pervious to gases. Welds inside the bag together with the perimeter weld define a pathway through which gases can flow from the interior of the bag to the vent. This pathway includes one or more vents through which gases must pass before they reach the vent. These gateways are sufficiently narrow at least substantially to prevent the passage of solid materials and liquids. If desired, the welds can be discontinuous to provide a multiplicity of gateways.

4 Claims, 3 Drawing Figures

SURGICAL COLLECTION BAGS

BACKGROUND OF THE INVENTION

Surgical collection bags intended for post operative use such as following colostomy of ileostomy operations are frequently called "ostomy bags". This term will be used herein.

As is well known, such bags are commonly made of flexible plastics material and have an inlet opening in one wall. The stoma of the patient is entered in this opening. The inlet opening is surrounded by a suitable seal which can adhere to the body of the patient. Various means are used for securing the bags to the body of the patient. The bags receives, through the stoma of the patient and the inlet opening of the bag, liquid and solid material from the intestine of the patient. The flow of such material into the bag is outside the control of the patient. In addition to such liquid and solid material, flatus will also enter the bag from the patient and will inflate the bag unless it is permitted to escape. Bags of this kind are, therefore, often provided with a vent near what is the top of the bag when it is in use. The vent often includes a deodorising filter. However, the liquid or solid material can block the vent with the result that the bag begins undesirably to inflate. An object of the present invention is to provide a way of avoiding this disadvantage.

BRIEF SUMMARY OF THE INVENTION

Accordingly, the present invention provides a surgical collection bag having two opposed walls secured together at their perimeter, an inlet into the bag through one of the walls and a vent which is impervious to solid matter and liquid but which is pervious to gases, wherein the bag has means defining a pathway to the vent including a gateway through which gases must pass, the said gate being sufficiently narrow at least substantially to prevent the passage of solid material and liquid. It is preferred that the bag has a plurality of gateways leading to the vent. The gateway or gateways may be formed by one or more welds between the opposing walls of the bag. The welds may be discontinuous to provide a multiplicity of gateways, each break in each discontinuous weld being a gateway.

BRIEF DESCRIPTION OF THE ACCOMPANYING DRAWINGS

Figure 2:
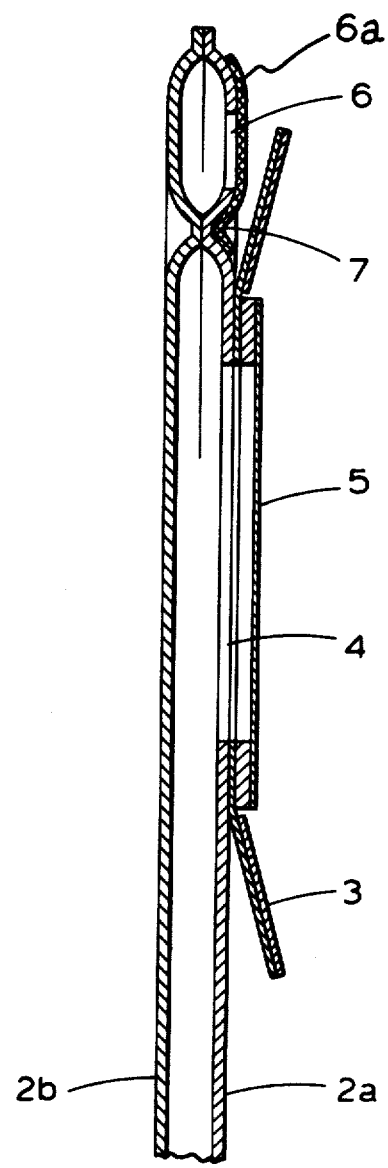
Figure 3:
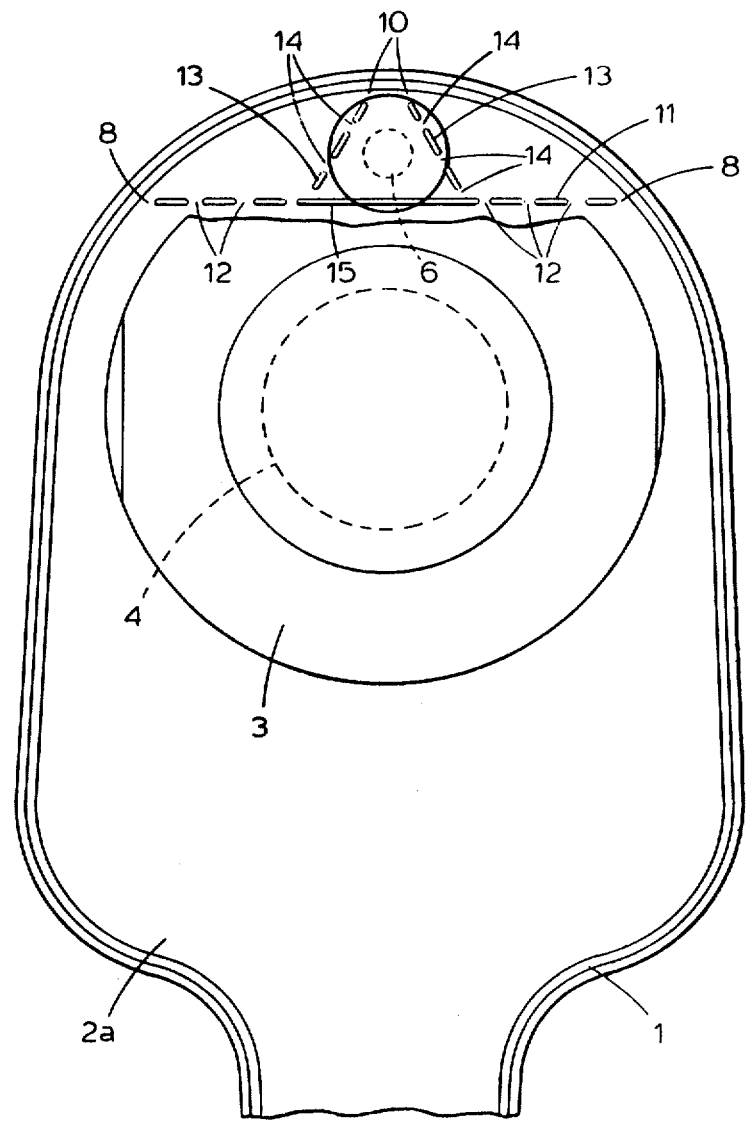

In the accompanying schematic drawings:

FIG. 1 is an elevation of one face of an ostomy bag constructed according to one embodiment of the invention, FIG. 2 is a longitudinal sectional view, and FIG. 3 is a view similar to FIG. 1 and illustrating a modification.

DESCRIPTION OF SOME EMBODIMENT OF THE INVENTION

The ostomy bag illustrated in FIGS. 1 and 2 comprises two sheets of a flexible plastics material. These sheets are welded together by a perimeter weld 1 to form the walls 2a, 2b of the bag. One of the walls (2a) is attached to a fixing flange 3 by which the bag can be secured to the body of the patient. The wall 2a of the bag has an inlet opening 4 within the fixing flange 3. A seal 5 capable of adhering to the body is provided at the inlet opening. This seal 5 may either be in the form of a ring or it can (as shown) be in the form of a disc in which a suitable opening can be made by the patient to enable his stoma to pass through the inlet opening 4 so that the contents of his intestine can flow into the interior of the bag. A vent 6 with a deodorising filter 6a is provided in the wall 2a of the bag at a position which will be near the top of the bag when it is in use on the patient.

The present invention provides a baffle which will hinder the passage of liquid or solid material from the interior of the bag to the filter 6 but will not hinder the passage of flatus. The baffle of the invention is provided by a plurality of welds between the opposite walls of the bag. Thus, in this embodiment there is a linear weld 7 extending transversely across the bag just below the vent 6/filter 6a, i.e. between the vent 6 and the filter 6a and the inlet opening 4, but the weld may be broken as hereinafter to be described with reference to FIG. 3 and/or it may be curved. This weld 7 terminates at each end a short distance from the perimeter weld 1 of the bag to provide two gateways 8 (FIG. 1), one at each end of the weld 7. Thus, material entering the bag through the inlet opening 4 cannot reach the vent 6 without going through the gateways 8 because the weld 7 is arranged between the inlet opening 4 and the vent 6. Two additional welds 9 run from the transverse weld 7 towards the edge of the bag which is at the top when the bag is in use and converging towards the centre line of the bag. It is not essential for the welds 9 to converge as they may have any suitable disposition relative to the weld 7. Gaps between the ends of these welds and the weld 1 at the perimeter of the bag provide additional gateways 10 through which material which has passed through the gateways 8 must pass before it can reach the filter.

Thus, the various welds and gateways provide a tortuous pathway between the main portion of the bag entered by the inlet opening 4 and the filter 6a. Flatus can pass through these gateways easily but they impede the passage of solid and liquid material and therefore reduce the possibility of the filter 6a becoming blocked so that its venting capability is not impaired.

A modification of the ostomy bag illustrated in FIGS. 1 and 2 is illustrated in FIG. 3 in which like parts are designated by the same reference numerals. In this modification, the continuous weld 7 of the arrangement illustrated in FIG. 1 is replaced by a discontinuous weld 11. The gaps or breaks in this discontinuous weld produce a multiplicity of gateways 12. Likewise the continuous weld 9 of the FIG. 1 construction is replaced by a discontinuous weld 13 the breaks or gaps in which provide a multiplicity of gateways 14. The central portion 15 of the weld 11 in this modification may be a continuous weld as illustrated in the drawings, but it may alternatively be a discontinuous or broken weld.

It will be appreciated that instead of a discontinuous weld of linear or curvilinear form, a multiplicity of gateways may be obtained by welds arranged to define a stepped or maze formation.

All the bags described may be modified by the arrangement of an intermediate sheet of plastics material (not illustrated) between the walls 2a and 2b. This intermediate sheet extends to just below the vent 6 and the welds producing the gateways are made between this intermediate sheet and the wall 2a.

What is claimed is:

1. A surgical collection bag having two opposed walls secured together at their perimeter, one of said walls having a first opening in the surface thereof to provided an inlet into said bag, a second opening in said one of said walls spaced above said first opening to provide a vent for the passage of gases to the environment, a weld positioned between said first and second openings and connecting together said opposed walls to provide a seal interposed between said first and second openings, said seal having at least two spaced openings therein of preselected length to substantially prevent the passage of solid and liquid material therethrough, and a deodorizing filter covering said vent said opposed walls being secured together by a perimeter weld, a first internal weld extends across the bag between the inlet and the vent to secure the opposed walls together, the said first weld having ends spaced from the perimeter weld to provide at each end of the weld a gateway through which gases may pass, further internal welds running from the first internal weld towards the perimeter weld with the vent between them, the said further welds having ends spaced from the perimeter weld to provide additional gateways through which gases may pass before reaching the vent.

2. In a surgical collection bag having two opposed walls secured together at their perimeter, an inlet to the bag through one of the walls and a vent which is impervious to solid matter and liquid but which is pervious to gases, the improvement in which the bag has means defining an internal passageway to the vent including a gateway through which gases must pass, the said gateway being sufficiently narrow at least substantially to prevent the passage of solid material and liquid, said opposed walls being secured together by a perimeter weld, a first internal weld extends across the bag between the inlet and the vent to secure the two walls together, the said first internal weld being discontinuous so as to define a multiplicity of gateways through which gases may pass, two further internal welds running from the first discontinuous weld towards the perimeter weld with the vent between them, the said further welds being also discontinuous to provide a further multiplicity of gateways through which gases may pass before reaching the vent.

3. A surgical collection bag having two opposed walls secured together at their perimeter, one of said walls having a first opening in the surface thereof to provide an inlet into said bag, a second opening in said one of said walls spaced above said first opening to provide a vent for the passage of gases to the environment, a weld positioned between said first and second openings and connecting together said opposed walls to provide a seal interposed between said first and second openings, said seal having at least two spaced openings therein of preselected length to substantially prevent the passage of solid and liquid material therethrough, and a deodorizing filter covering said vent.

4. A bag as in claim 3, in which said weld defines a tortuous path between said first and second openings.

* * * * *